(12) United States Patent
Quaedflieg et al.

(10) Patent No.: US 8,450,084 B2
(45) Date of Patent: May 28, 2013

(54) CHEMO-ENZYMATIC PEPTIDE SYNTHESIS VIA C-TERMINAL ESTER INTERCONVERSION

(75) Inventors: Peter Jan Leonard Mario Quaedflieg, Elsloo (NL); Timo Nuijens, Maastricht (NL); Claudia Cusan, Aachen (DE); Harold Monro Moody, Gulpen (NL); Theodorus Johannes Godfried Maria Van Dooren, Roermond (NL)

(73) Assignee: Enzypep B.V., Geleen (NL)

( * ) Notice: Subject to any disclaimer, the term of this patent is extended or adjusted under 35 U.S.C. 154(b) by 0 days.

(21) Appl. No.: 12/682,653

(22) PCT Filed: Oct. 9, 2008

(86) PCT No.: PCT/EP2008/063574
§ 371 (c)(1),
(2), (4) Date: Aug. 9, 2010

(87) PCT Pub. No.: WO2009/047311
PCT Pub. Date: Apr. 16, 2009

(65) Prior Publication Data
US 2010/0311113 A1     Dec. 9, 2010

(30) Foreign Application Priority Data
Oct. 12, 2007   (EP) .................................. 07020031

(51) Int. Cl.
*C12P 21/06*     (2006.01)
*C12P 7/62*      (2006.01)

(52) U.S. Cl.
USPC ........................................ 435/68.1; 435/135

(58) Field of Classification Search
None
See application file for complete search history.

(56) References Cited

FOREIGN PATENT DOCUMENTS
WO   WO 2007/045470   4/2007
WO   WO 2007/082890   7/2007

OTHER PUBLICATIONS

Yamamoto et al. Catalysis of enzyme aggregates in organic solvent. An attempt at evaluation of intrensic activity in ethanol. Biotechnology Letters 1993, 15 (6), 647-652.*
International Search Report for PCT/EP2008/063574, mailed Jan. 19, 2009.
Liu, C.F. et al., "Subtilisin-catalyzed synthesis of amino acid and peptide esters. Application in a two-step enzymatic ligation strategy", Organic Letters, vol. 3, No. 26 (Nov. 29, 2001), pp. 4157-4159.
Ferjancica, A. et al., "Subtilisin-Catalysed Peptide Synthesis and Transesterification in Organic Solvents", Applied Microbiology and Biotechnology, vol. 32, No. 6, (Mar. 1990), pp. 651-657.
Santos et al, "Effect of Crown Ethers on Structure, Stability, Activity, and Enantioselectivity of Subtilisin Carlsberg in Organic Solvents", Biotechnology and Bioengineering 74(4):295-308 (2001).
Barbas et al, "A Search for Peptide Ligase: Cosolvent-Mediated Conversion of Proteases to Esterases for Irreversible Synthesis of Peptides", J. Am. Chem. Soc. 110:5162-5166 (1988).
Ferjancic et al, "Subtilisin-catalysed peptide synthesis and transesterification in organic solvents", Appl. Microbiol. Biotechnol. 32:651-657 (1990).

* cited by examiner

*Primary Examiner* — Nashaat Nashed
(74) *Attorney, Agent, or Firm* — Nixon & Vanderhye P.C.

(57) ABSTRACT

The invention relates to a method for preparing an optionally N-protected amino acid C-terminal ester or an optionally N-protected peptide C-terminal ester, comprising transesterifying the C-terminal t-alkyl ester of the amino acid or the C-terminal t-alkyl ester of the peptide with an alcohol (other than the t-alcohol corresponding to the t-alkyl group of the ester) in the presence of a hydrolytic enzyme (E.C. 3).
The invention further relates to a method for preparing a peptide comprising coupling an activated, N-protected, amino acid C-terminal ester or an optionally N-protected peptide C-terminal ester with an optionally C-terminal protected amino acid or an optionally C-terminal protected peptide via a peptide bond, in the presence of an enzyme catalysing peptidic bond formation.

16 Claims, 6 Drawing Sheets

CHEMO-ENZYMATIC PEPTIDE SYNTHESIS VIA C-TERMINAL ESTER INTERCONVERSION

This application is the U.S. national phase of International Application No. PCT/EP2008/063574 filed 9 Oct. 2008, which designated the U.S. and claims priority to EP Application No. 07020031.6 filed 12 Oct. 2007, the entire contents of each of which are hereby incorporated by reference.

The invention relates to a method for preparing a peptide comprising coupling an activated, N-protected, amino acid C-terminal ester or an optionally N-protected peptide C-terminal ester. The invention further relates to a method for preparing an N-protected amino acid C-terminal ester or an optionally N-protected peptide C-terminal ester.

Peptides, in particular oligopeptides have many applications, for instance as pharmaceutical, food or feed ingredient, agrochemical or cosmetic ingredient.

For the purpose of this invention, with peptides is meant any chain of two or more amino acids. For the purpose of this invention, with 'oligopeptides' is meant a peptide based on 2-200 amino acids, in particular based on 2-100, more in particular based on 2-50 amino acids, preferably any linear chain of 2-200 amino acids, more preferably of 2-100 or 2-50 amino acids. The term 'polypeptides' is used for peptides based on a higher number of amino acids than specified for oligopeptides.

Chemo-enzymatic peptide synthesis, which is defined for the purpose of the invention as the synthesis of peptides in which peptidic bonds are formed by an enzymatic coupling reaction, has several advantages over chemical peptide synthesis. For instance, the cost-price in case of large scale production is lower due to the fact that no or limited amino acid side chain protection is required. Also, the process is more environmentally friendly. For instance, no stoichiometric amounts of toxic chemical reagents, such as dicyclohexyl carbodiimide (DCC), 1-(3-dimethylaminopropyl)-3-ethylcarbodiimide hydrochloride (EDC) or 1-(3-dimethylaminopropyl)-3-ethylcarbodiimide methiodide (EDCl), are required. Further, such method may be carried out using less organic solvent. Furthermore, enzyme-catalyzed couplings are devoid of racemisation (see for instance Sewald and H.-D. Jakubke, in: "Peptides: Chemistry and Biology", 1$^{st}$ reprint, Ed. Wiley-VCH Verlag GmbH, Weinheim 2002, p 250) leading to more pure products and/or easier isolation.

With respect to the chemo-enzymatic coupling method there are two options to generate the peptidic bond. In the so-called thermodynamic (or equilibrium-controlled) approach, the carboxy component bears a free carboxylic acid functionality, while in the kinetically controlled approach an activated carboxy component is used, preferably in the form of an alkylester, for example in the form of a methylester.

The term 'activated' is used to indicate that the C-terminal carboxyl group shows substantial reactivity, in particular higher reactivity compared to a C-terminal protected carboxyl group, such as a C-terminal t-alkyl ester, in a kinetic enzymatic coupling reaction wherein an amino acid or peptide is coupled to the C-terminal carboxy group. Activated ester groups in particular include C-terminal optionally substituted n-alkyl-esters, such as optionally substituted methyl esters, ethyl esters, n-propyl esters, n-butyl esters, etc.; aralkyl esters, in particular optionally substituted benzyl esters; and optionally substituted aryl esters, in particular optionally substituted phenyl esters of an amino acid or peptide. Substituents may in particular be selected from the group of optionally protected functional groups comprising one or more heteroatoms such as oxygen, sulphur and nitrogen. Examples thereof include hydroxyl groups, thiol groups and amine groups.

The thermodynamic approach has three major disadvantages: i) the equilibrium is usually on the side of peptide bond cleavage so that the coupling yields are poor; ii) a large amount of enzyme is usually required; iii) the reaction rates are usually very low. In the kinetically controlled approach alkyl esters are required as starting material but much less enzyme is required, the reaction time is significantly shorter, and, above all, the maximum obtainable yields are usually considerably higher. Therefore, for industrial application, an enzymatic peptide synthesis concept based on a kinetic approach, i.e. using an activated carboxy component, is most attractive (see for instance N. Sewald and H.-D. Jakubke, in: "Peptides: Chemistry and Biology", 1$^{st}$ reprint, Ed. Wiley-VCH Verlag GmbH, Weinheim 2002, section 4.6.2).

Chemo-enzymatic peptide synthesis can be performed in the C→N terminal direction or in the N→C terminal direction.

An example of chemo-enzymatic peptide synthesis in the C→N terminal direction is given in Scheme 1.

In Scheme 1, P stands for an N-terminal protecting group. $R^1$, $R^2$ and $R^3$ each independently stand for an amino acid side chain. As is indicated by Scheme 1, the enzymatic synthesis in the C→N terminal direction starts with an enzymatic coupling of a C-terminal protected amino acid of formula II to an N-protected amino acid of formula Ia, the latter being C-activated, in this case by a methyl ester.

The term 'C-terminal protected' is used herein to indicate that a C-terminal carboxyl-group is provided with a protec- tive group, generally substantially protecting the carboxyl group from being coupled to an amine group of another molecule. In particular, the C-terminal protected group may be a C-terminal ester whereby the C-terminal carboxyl group is at least substantially protected from being coupled to an amine under peptide synthesis conditions used. In general, t-alkyl is used as protective group in a method according to the invention.

The term 'N-terminal protected' is used herein to indicate that an N-terminal amine group is provided with a protective group, generally at least substantially protecting the N-terminal amine group from participating in coupling of a C-terminal carboxyl group to the N-terminal amine group.

The formed peptide of formula III may then be N-deprotected and the resulting peptide of the formula IV, bearing a free amino function, may subsequently be coupled enzymatically to another N-protected (and C-activated) amino acid building block of formula Ib resulting in the formation of a peptide of formula V. This N-deprotection and coupling cycle may be repeated until the desired peptide sequence is obtained, after which the N- and C-terminal protecting groups may be removed to give the desired (unprotected) peptide. Of course it is also possible to couple the N-protected amino acid of formula Ia with a C-terminal protected peptide instead of with the C-terminal protected amino acid of formula II.

A main disadvantage of the synthesis of peptides in the C→N terminal direction is that the N-protecting group is removed after each cycle to allow addition of a further N-protected amino acid residue. The introduction of an (expensive) N-protecting group on an amino acid (ester) and the removal and usually disposal of this same (expensive) N-protecting group after the peptide coupling, make synthesis of peptides in the C→N direction unattractive from a practical and economical point of view.

An example of enzymatic peptide synthesis in the N→C terminal direction is given in Scheme 2.

X = e.g. NH$_2$, O—$^t$Bu

In Scheme 2, P stands for an N-terminal protecting group. R$^1$, R$^2$ and R$^3$ each independently stand for an amino acid side chain. As is indicated in Scheme 2, enzymatic synthesis in the N→C terminal direction also starts with an enzymatic coupling of a C-terminal protected amino acid of formula IIa with an N-protected amino acid of formula I, the latter compound being C-activated, in this case by a methyl ester. The formed dipeptide of formula III may then be C-deprotected (see below).

The resulting dipeptide of formula VI, bearing a free carboxylic acid function, may then be "reactivated" to form an N-protected peptide C-terminal alkylester of the formula VII, in the case of Scheme 2 a methyl C-terminal ester. This esterification is typically executed by a chemical transformation using an alcohol (for instance methanol) and a reagent such as sulphuric acid or thionyl chloride. The N-protected peptide alkylester of formula VII may subsequently be coupled with another C-terminal protected amino acid of formula IIb which will result in the formation of a tripeptide of formula VIII. This C-deprotection and coupling cycle may be repeated until the desired amino acid sequence is obtained, after which the N-terminal and C-terminal protective groups may be removed to give the desired (unprotected) peptide. Of course it is also possible to couple the N-protected amino acid of formula I with a C-terminal protected peptide instead of with the C-terminal protected amino acid of formula IIa.

Synthesis of peptides in the N→C terminal direction does not require the repeated addition and removal of an (expensive) N-protecting group. However, in order to allow the addition of a further amino acid residue, two reaction steps are needed: the C-terminus needs to be selectively deprotected, after which it should be selectively activated, for instance by esterification of the formed carboxylic acid group. Therefore, in total three reaction steps (deprotection, activation and coupling) are needed for the addition of one amino acid residue to an N-protected peptide for peptide synthesis in the N→C terminal direction.

Suitable C-terminal deprotection methods for the peptide of formula III may be selected depending on the protective group X used. For instance in case X is t-butyl or another tertiary alkyl, the t-alkyl group is typically cleaved off chemically, using a strong acid, in particular trifluoroacetic acid (TFA).

C-terminal t-alkyl deprotection by using TFA can lead to various side reactions in the growing peptide chain, in particular if traces of water are present. Examples of such side reactions are t-alkylation of a side chain group, deprotection of a side chain group, N-deprotection and hydrolysis of acid labile functionalities, for instance hydrolysis of a peptidic bond.

Complete or almost complete removal of TFA is laborious (and expensive) but of crucial importance in case the C-terminal carboxylic acid is to be reactivated, such as for use in an enzymatic coupling with a next C-terminal protected amino acid.

Therefore, in the art it is considered to be advantageous to use carboxyamide as a C-terminal protective group (X=NH$_2$ in Scheme 2). With carboxyamide as a protective group the amino acid building blocks of formula IIa may for example be prepared by methylesterification of the amino acid followed by an amidation with ammonia in a 1-pot process, which preparation is simple and cost-effective. Carboxyamide cleavage by conventional means, using an aqueous solution of a strong mineral acid, causes simultaneous partial cleavage of peptidic bonds. However, selective deprotection of a carboxyamide protected C-terminus of a peptide without cleaving peptidic bonds may be done enzymatically. EP-A 0 456 138 and EP-A 0 759 066 disclose an enzymatic process using a peptide amidase from the flavedo of oranges or from *Xanthomonas* (*Stenotrophomonas*) *maltophilia*, respectively, wherein the carboxyamide group of an N-(un)protected dipeptide C-terminal carboxyamide is hydrolysed to form the corresponding C-terminal carboxylic acid, whereby the peptidic bond of the dipeptide is left intact.

A disadvantage of the process as described in EP-A 0 456 138 and EP-A 0 759 066, however, is that separate esterification of the formed corresponding carboxylic acid—in order to activate the carboxylic acid group—is required for each further elongation of the peptide chain with an amino acid. Another disadvantage is that this esterification of the carboxylic acid in the presence of a reagent such as sulphuric acid or thionyl chloride requires essentially non-aqueous conditions, whereas the enzymatic deprotection reaction of the C-terminal carboxyamide is performed in aqueous solution. Thus, extensive extraction and drying operations are required.

In an improved method, as disclosed in WO 2007/045470, such disadvantages are overcome by using a specific enzyme to react a peptide C-terminal carboxyamide with an alkyl alcohol in the presence of a peptide amidase. The peptide amidase may in particular be from the flavedo of citrus fruits and is generally not readily available in large quantities. For the peptide amidase to be active, the reaction is preferably carried out in the presence of water, generally more than 0.5 wt. %, most preferably at least 5 wt. %. Moreover, ammonia is formed. A complexing agent for the ammonia is mostly required to remove ammonia during the reaction, to draw the equilibrium of the reaction towards the side of the ester synthesis. Addition of extra reagents or aids for carrying out the reaction make the system more complicated and/or may introduce impurities in the product.

There remains a need for alternative methods for peptide synthesis and/or for preparing intermediate compounds that can be used for peptide synthesis. Such methods may, e.g., provide additional methodology that increases flexibility in peptide synthesis and/or allow the synthesis of specific peptides that are not or relatively difficult to obtain using known methodology.

In particular there remains a need for relatively simple methods that are relatively environmentally friendly.

It would also be desirable to provide a relatively simple method wherein an a C-terminal t-alkyl ester of an amino acid or peptide, in particular a peptide C-terminal t-butyl ester thereof, can be converted into another C-terminal ester without needing to chemically hydrolyse the C-terminal ester to be converted.

In particular, it would be desirable to provide a method wherein an amino acid C-terminal ester or a peptide C-terminal ester can be prepared from an amino acid C-terminal ester or a peptide C-terminal ester different from the amino acid ester respectively peptide ester to be prepared, with high yield (within an acceptable reaction time) and/or good selectivity. This would be especially desirable for using such method in the preparation of a peptide, in particular such a peptide for use as a pharmaceutical, a food or feed ingredient, an agrochemical or a cosmetic ingredient or such a peptide for use in the manufacture of a pharmaceutical, a food or feed ingredient, an agrochemical or a cosmetic ingredient.

It has now been found possible to obtain an N-protected amino acid C-terminal ester or a peptide C-terminal ester, in particular a C-activated N-protected amino acid or a C-activated peptide (which is optionally N-protected), by reacting an N-protected amino acid or an optionally N-protected peptide of which the C-terminal carboxyl group has been protected with a t-alkyl group, in the presence of a specific enzyme.

It has further been found that a peptide can be synthesized by coupling an amino acid or peptide to another amino acid or peptide in the N→C terminal direction, without requiring chemical C-terminal deprotection and subsequent chemical activation of the carboxylic acid function.

Accordingly, the present invention relates to a method for preparing a peptide comprising coupling an activated, N-protected, amino acid C-terminal ester or an activated optionally N-protected peptide C-terminal ester comprising transesterifying a C-terminal ester of a first N-protected amino acid or a C-terminal ester of a first optionally N-protected peptide with an activating alcohol in the presence of a hydrolytic enzyme, thereby forming a second N-protected amino acid C-terminal ester or a second optionally N-protected peptide C-terminal ester; and coupling the second ester with an optionally C-terminal protected amino acid or an optionally C-terminal protected peptide forming a peptidic bond, in the presence of a hydrolytic enzyme catalysing peptidic bond formation, which enzyme may be the same as or different from the enzyme used for the transesterification.

Usually, the C-terminal ester of the first amino acid or of the first peptide is a t-alkyl ester.

The invention further relates to a method for preparing a peptide comprising activating a C-terminal carboxylic acid group—or a salt thereof—of an N-protected amino acid or an optionally N-protected peptide or salt thereof, with an activating alcohol, in the presence of a hydrolytic enzyme, and coupling an optionally C-terminal protected amino acid or an optionally C-terminal protected peptide to the activated amino acid or peptide, in the presence of a hydrolytic enzyme, which enzyme may be the same as or different from the enzyme used for the activation.

The term 'activating alcohol' is used herein for an alcohol of which provides an activated C-terminal carboxy ester group, after (trans)esterification.

The C-terminal protected amino acid or peptide usually is a t-alkyl ester, although in particular in case the final product is a dipeptide, the C-terminal group may in principle be protected with another protecting group.

The enzyme catalysing peptidic bond formation may be different from the enzyme used for the transesterification, or the same if the latter is capable of catalysing peptidic bond formation.

The invention further relates to a method for preparing an N-protected amino acid C-terminal ester or an optionally N-protected peptide C-terminal ester, comprising transesterifying a C-terminal t-alkyl ester of the N-protected amino acid or a C-terminal t-alkyl ester of the optionally N-protected peptide with an alcohol—other than the t-alkyl alcohol corresponding to the t-alkyl group of the first ester—in the presence of a hydrolytic enzyme.

A compound that is to be enzymatically activated, esterified or transesterified may hereinafter be referred to as the 'substrate', unless specified otherwise.

It is noted that Liu and Tam report in 'Organic Letters, 2001, Vol 3, No. 26, p 4157-4159' that subtilisin Carlsberg is capable of catalysing the formation of C-alpha-carbonyl 3 hydroxypropyl or 4 hydroxybutyl esters of certain Boc-amino acids and peptides, of which the C-terminal carboxylic acid function is unprotected, in 1,3-propanediol and in 1,4-butaned diol. It is not disclosed to prepare a peptide by a method wherein an amino acid C-terminal t-alkyl ester or a peptide C-terminal t-alkyl ester is activated and then coupled with another amino acid or peptide.

Surprisingly, it has been found that a hydrolytic enzyme can be used for transesterification of the t-alkyl ester (t-alkyl groups being suitable protective groups for a carboxylic acid function, and thereby being particularly useful in peptide synthesis), to a different ester group, in particular an activated ester group.

In particular it is surprising that a hydrolytic enzyme, more in particular a single hydrolytic enzyme, may be used both for transesterification of a protected ester into an activated ester, and coupling of an activated amino acid or peptide to another amino acid or peptide. It is in particular surprising that the transesterification yield is high enough to allow efficient synthesis of a peptide, making use of a hydrolytic enzyme in accordance with the invention.

The transesterification in accordance with the invention thus in particular not only offers an advantage in that it provides a way to deprotect a t-alkyl protected terminal carboxyl group, a protective group with good protective properties, without needing a strong acid such as TFA, which is disadvantageous for the reasons given above, but furthermore in that C-deprotection of a t-alkyl protected terminal carboxyl group and C-activation are combined in essentially one step, or at least may take place catalysed by a single enzyme. In particular, it has been found possible to realise both deprotection and activation in one step with a high yield (i.e. number of moles of activated ester at the end of the reaction/initial number of moles of C-terminal protected ester).

Moreover, it has been found possible to carry out the invention on an industrial scale.

In an advantageous embodiment, the method of the invention allows transesterification of a first ester into a second ester in a high yield, in particular of at least 70%, more in particular of at least 80%, even more in particular of at least 90%.

The t-alkyl may in principle be any protective tertiary alkyl group. Preferably the t-alkyl is selected from the group of t-butyl (2-methyl-2-propyl), t-pentyl (2-methyl-2-butyl) and t-hexyl (2,3-dimethyl-2-butyl). Good results have in particular been achieved with t-butyl.

The term 'hydrolytic enzyme' is used herein for enzymes from the classification group E.C. 3. Preferably, one or more hydrolytic enzymes are used selected from the group of carboxylic ester hydrolases (E.C. 3.1.1), thiolester hydrolases (E.C. 3.1.2) and peptidases (E.C. 3.4).

In particular a peptidase (E.C. 3.4) may be used. Preferred peptidases are peptidases selected from the group of serine-type carboxypeptidases (E.C. 3.4.16), metallocarboxypeptidases (E.C. 3.4.17), cysteine-type carboxypeptidases (E.C. 3.4.18), serine endopeptidases (E.C. 3.4.21), cysteine endopeptidases (E.C. 3.4.22), aspartic endopeptidases (E.C. 3.4.23) and metalloendopeptidases (E.C. 3.4.24), in particular from serine endopeptidases (E.C. 3.4.21). In particular good results have been achieved with a subtilisin (E.C. 3.4.21.62), such as subtilisin Carlsberg.

The hydrolytic enzyme may be used in any form. For example, the hydrolytic enzyme may be used—for example in the form of a dispersion, emulsion, a solution or in immobilized form (for instance loaded on a support, e.g. a particulate or monolithic carrier material)—as crude enzyme, as a commercially available enzyme, as an enzyme further purified from a commercially available preparation, as an enzyme obtained from its source by a combination of known purification methods, in whole (optionally permeabilised and/or immobilised) cells that naturally or through genetic modification possess hydrolytic activity, or in a lysate of cells with such activity.

The hydrolytic enzyme may be obtained or derived from any organism, in particular from an animal, plant, bacterium, a mould, a yeast or fungus.

It will be clear to the average person skilled in the art that use can also be made of mutants of naturally occurring (wild type) enzymes with hydrolytic activity in the process according to the invention. Mutants of wild-type enzymes can for example be made by modifying the DNA encoding the wild-type enzymes using mutagenesis techniques known to the person skilled in the art (random mutagenesis, site-directed mutagenesis, directed evolution, gene shuffling, etc.) so that the DNA encodes an enzyme that differs by at least one amino acid from the wild-type enzyme or so that it encodes an enzyme that is shorter compared to the wild-type and by effecting the expression of the thus modified DNA in a suitable (host) cell. Mutants of the hydrolytic enzyme may have improved properties, for instance with respect to one or more of the following aspects: selectivity towards the substrate, activity, stability, solvent resistance, pH profile, temperature profile, substrate profile.

When referring to an enzyme from a particular source, recombinant enzymes originating from a first organism, but actually produced in a (genetically modified) second organism, are specifically meant to be included as enzymes from that first organism.

Examples of organisms from which the hydrolytic enzyme may be derived include *Trichoderma* sp, such as from *Trichoderma reesei*; *Rhizopus* sp., such as from *Rhizopus oryzae*; *Bacillus* sp, such as from *Baccillus licheniformis, Bacillus subtilis Bacillus amyloliquefaciens, Bacillus clausii, Bacillus lentus, Bacillus alkalophilus, Bacillus halodurans; Aspergillus* sp., such as from *Aspergillus oryzae* or *Aspergillus niger*; *Streptomyces* sp., such as from *caespitosus Streptomyces* or *Streptomyces griseus*; *Candida* sp.; fungi; *Humicola* sp; *Rhizoctonia* sp.; *Cytophagia*; *Mucor* sp.; and animal tissue, in particular from pancreas, such as from porcine pancreas, bovine pancreas or sheep pancreas.

As indicated above, a preferred enzyme is subtilisin. Various subtilisins are known in the art, see e.g. U.S. Pat. No. 5,316,935 and the references cited therein. Subtilisin A is a commercially available subtilisin from Novozymes.

Particularly preferred is subtilisin Carlsberg.

Alcalase® has been found to be particularly suitable for use in a method of the invention. This product is available from Novozymes (Bagsvaerd, Denmark). Alcalase® is a cheap and industrially available proteolytic enzyme mixture produced by *Bacillus licheniformis* (containing subtilisin Carlsberg as a major enzyme component). Experiments with purified subtilisin confirmed that subtilisin catalyses transesterification, activation and peptidic bond formation.

Commercially available enzyme, such as Alcalase®, may be provided by the supplier as a liquid, in particular an aqueous liquid. In such case, the enzyme is preferably first isolated from undesired liquid, for instance excess water, alcohols that cause an undesired side-reaction, in particular undesired transesterification, and the like. This may suitably be accomplished by precipitating, usually followed by separation of the solid from the liquid, and/or drying. Precipitation may be accomplished using an alcohol, such as t-butanol or an alcohol used in the method of the invention. In case another alcohol is used, care should be taken that such alcohol does not interfere adversely with the C-terminal transesterification or another reaction step.

The enzyme may thereafter be dissolved and/or resuspended in an alcohol, such as t-butanol or an alcohol used in the method of the invention.

It is noted that the enzymatic hydrolysis of C-terminal t-butyl esters of peptides is known. For instance, WO 2007/082890 refers to the use of BsubpNBE, CAL-A or subtilisin to hydrolyse such esters. However it is surprising that the thermodynamically unfavourable opposite esterification reaction or the transesterification of a t-alkyl ester to a primary or secondary alkyl ester or an optionally substituted aralkyl ester or an optionally substituted aryl ester can efficiently be accomplished with a hydrolytically active enzyme. It is especially surprising that yields of more than 80% are feasible.

Other suitable hydrolytic enzymes may be selected from the group of the following commercially available products, and functional analogues of such enzymes. With functional analogues is meant that the analogue is capable of catalysing at least one of the functions: transesterification, activation and formation of a peptide bond (peptide coupling) in a method of the invention, preferably two or all three of these functions.

Novozymes (Bagsvaerd, Denmark) offers ovozyme, liquanase, Alcalase®, Alcalase-Ultra® (in particular effective at alkaline pH), duramyl, esperase, kannase, savinase, savinase ultra, termamyl, termamyl ultra, novobate, polarzyme, neutrase, novoline, pyrase, novocor (bacterial alkaline proteases).

Proteinase-K is available from New England Biolabs, Ipswich (MA), USA.

Novo Nordisk Biochem North America Inc (Franklinton N.C., USA) offers Protease *Bacillus* species (Esperase 6.0 T; Savinase 6.0 T), Protease *Bacillus subtilis* (Neutrase 1.5 MG), Protease *Bacillus licheniformis* (Alcalase 3.0 T).

Amano International Enzyme Co (Troy, Va., USA) offers Protease *Bacillus subtilis* (Proleather; Protease N) and Protease *Aspergillus oryzae* (Prozyme 6).

It is possible to carry out the reaction in a mixture comprising the alcohol for the (trans)esterification or activation and optionally an inert organic solvent, for instance acetonitrile or an ether, such as methyl-t-butyl ether (MTBE).

Carrying out the (trans)esterification or activation in a mixture comprising said alcohol and an inert solvent is in particular advantageous in case the alcohol adversely affects the stability or activity of the enzyme. The concentration of the alcohol for the (trans)esterification or activation may in particular be 99.9 wt. % or less (based on total liquids), 99 wt. % or less, 95 wt. % or less, 75 wt. % or less, 50 wt. % or less, 30 wt. % or less 20 wt. % or less or 10 wt. % or less.

In particular for methanol it has been found advantageous to use methanol in a mixture with another (inert) organic solvent as the major solvent, for a good enzyme stability, i.e. maintaining substantial enzymatic activity for a sufficient time to obtain the ester to be prepared in a desired yield.

Usually, the concentration of the alcohol for the (trans) esterification or activation is at least 0.1 wt. %, in particular at least 0.5 wt. %, preferably at least 1 wt. %, at least 2 wt. %, or at least 4 wt. %, for an advantageous reaction rate.

A method of the invention may be carried out using a reaction medium wherein the alcohol for the esterification, the transesterification, or activation is the major solvent. As a major solvent, the concentration is usually 50-100 wt. %, based on total liquids, in particular up to 99.5 wt. %. The reaction medium is usually essentially free from other alcohols (than said alcohol and the t-alcohol that has been replaced from the C-terminal ester in case of transesterification) that may be detrimental to the reaction (which may compete with the alcohol in the reaction). In practice, a small amount of other alcohols may be present, for instance less than 5 wt. %, in particular less than 2 wt. %, more in particular less than 0.5 wt. %.

A method of the invention is usually carried out under substantially non-aqueous conditions. As the skilled person will understand, a small amount of water may be desired, depending upon the enzyme, to enable the enzyme to properly perform its catalytic activity. For a good catalytic activity the presence of a trace of water, e.g. of at least 0.01 wt. %, based on the liquid phase, may be desired. In particular, the water concentration may be at least 0.02 wt. % or at least 0.05 wt. %.

A desired upper limit for the water concentration depends on the specific enzyme, the nature of the peptide (e.g. size, the amino acids upon which the peptide is based), the desired final conversion and the desired transesterification or activation reaction rate.

The reaction medium usually contains, at least at the beginning of the activation or (trans)esterification less than 10 wt. % water, based on the weight of liquids in the reaction medium. The reaction medium may be dispersed in a second liquid phase or another liquid phase may be dispersed in the reaction medium. In case of a dual or multiphase system, the specified water content is based on the weight of liquids in the phase wherein the (trans)esterification or activation reaction—at least predominantly—takes place based on the liquid phase wherein the amino acid or peptide is dissolved.

In particular, the water concentration may be less than 4 wt. %, at least at the beginning of the activation or (trans)esterification. Advantageously, the method may be carried out in a medium containing less than 2 wt. % water, in particular 1 wt. % or less water, more in particular 0.5 wt. % or less water, for instance about 0.2 wt. % or less water, at least at the beginning of the reaction, whilst still retaining substantial desired enzyme activity and a low, or even undetectable, undesired hydrolysis.

In an advantageous method, an alcohol or water that is formed, in particular during (trans)esterification, may be removed continuously or intermittently. In principle removal may be accomplished in a manner known in the art. Good results have in particular been achieved using molecular sieves. Also very suitable for the removal is evaporation, such as be azeotropic removal using vacuum or distillation.

The amino acid C-terminal ester (which is N-protected, at least during the transesterification reaction) or the optionally N-protected peptide C-terminal alkylester may in particular be represented by a compound of formula IX.

IX

Herein P stands for H or for an N-terminal protecting group, wherein n is an integer of at least 1. In case n is 1, P usually is an N-terminal protecting group, because in the absence thereof the interconversion from one ester into another may be difficult to accomplish, depending on the enzyme used.

n may in particular be at least 2, at least 3, at least 4, at least 5, at least 6, at least 8, at least 9 or at least 10. n may in particular be 100 or less, 75 or less, 50 or less, 25 or less, 20 or less 15 or less or 10 or less, e.g. 5 or less.

Each $R^A$ and each $R^B$ independently represent H, or an organic moiety preferably an amino acid side chain. Thus, it is not required that $R^A$ is the same in all n amino acid units. Similarly, it is not required that $R^B$ is the same in all n amino acid units.

In case the formula IX represents an ester to be transesterified, R typically represents an optionally substituted t-alkyl, preferably t-butyl. The alkyl may in particular comprise a substituent containing a heteroatom, more in particular a heteroatom selected from the group of N, O and S. For instance the substituent may be an optionally protected hydroxyl, thiol or amine.

Suitable N-protecting groups are those N-protecting groups which can be used for the synthesis of (oligo)peptides. Such groups are known to the person skilled in the art. Examples of suitable N-protecting groups include carbonyl type protective groups, for instance 'Z' benzyloxycarbonyl), 'Boc' (i.e. t-butyloxycarbonyl), 'For' (i.e. formyl) and 'PhAc' phenacetyl), and FMOC (9-fluorenylmethoxycarbonyl). The groups For or PhAc may be introduced and cleaved enzymatically using the enzymes Peptide Deformylase or PenG acylase, respectively. Chemical cleavage methods are generally known in the art.

In the context of the invention with 'amino acid side chain' is meant any proteinogenic or non-proteinogenic amino acid side chain. The reactive groups in the amino acid side chains may be protected by amino acid side chain protecting groups or may be unprotected. Proteinogenic amino acids are the amino acids that are encoded by the genetic code. Proteinogenic amino acids include: alanine, valine, leucine, isoleucine, serine, threonine, methionine, cysteine, asparagine, glutamine, tyrosine, tryptophan, glycine, aspartic acid, glutamic acid, histidine, lysine, arginine, proline and phenylalanine.

Examples of non-proteinogenic amino acids are phenylglycine and 4-fluoro-phenylalanine.

In principle the pH used may be chosen within wide limits, as long as a pH is chosen at which the enzyme shows sufficient activity. Such a pH is usually known for the enzyme to be used, may be based on its known hydrolytic activity in an aqueous solution, or can be routinely determined, making use of a known substrate for the enzyme under known reaction conditions. It may in particular be chosen to be about neutral. If desired, alkaline or acidic conditions may be used, depending on the enzyme. If desired, the pH may be adjusted using an acid and/or a base or buffered with a suitable combination of an acid and a base. Suitable acids and bases are in particular those soluble in the reaction medium, e.g. from the group of ammonia and alcohol-soluble acids, e.g. acetic acid and formic acid. The pH of the reaction may be controlled by using an automated pH-stat system. Optimal pH conditions can easily be identified by a person skilled in the art through routine experimentation.

In principle the temperature used is not critical, as long as a temperature is chosen at which the enzyme shows sufficient activity and stability. Such a temperature is usually known for the enzyme to be used or can be routinely determined, making use of a known substrate for the enzyme under known reaction conditions. Generally, the temperature may be at least 0° C., in particular at least 15° C. or at least 25° C. In particular if an enzyme originating from a thermophilic organism is used, the temperature preferably is at least 40° C. A desired maximum temperature depends upon the enzyme. In general such maximum temperature is known in the art, e.g. indicated in a product data sheet in case of a commercially available enzyme, or can be determined routinely based on common general knowledge and the information disclosed herein. The temperature is usually 70° C. or less, in particular 60° C. or less or 45° C. or less. However, in particular if an enzyme from a thermophilic organism is used, the temperature may be chosen higher, for example up to 90° C.

Optimal temperature conditions can easily be identified for a specific enzyme by a person skilled in the art through routine experimentation based on common general knowledge and the information disclosed herein. For instance, for subtilisin, in particular subtilisin Carlsberg (e.g. in Alcalase®) the temperature may advantageously be in the range of 25-60° C.

As indicated above, the invention also provides a method for the preparation of a peptide. In particular, such method comprises the following steps:

An N-protected amino acid or an optionally N-protected peptide comprising a free terminal carboxylic acid group or a C-terminal t-alkyl ester is activated by converting the amino acid or peptide into an amino acid ester or peptide ester having an activated C-terminal carboxy group, using a hydrolytic enzyme as a catalyst. As a result, the amino acid C-terminal ester or peptide C-terminal ester is suitable for participating in a kinetic peptide coupling (the term "peptide coupling" means the coupling via formation of a peptide bond). Activation can in particular be done with an n-alkyl alcohol, in particular methanol, ethanol, n-propanol, n-butanol, etc., an optionally substituted aryl alcohol, such as phenol, or an optionally substituted aralkyl alcohol, such as benzyl alcohol.

Thereafter, the amino acid C-terminal ester or peptide C-terminal ester comprising the activated C-terminal carboxy group is contacted with an optionally C-terminal protected amino acid or peptide, usually in the presence of an enzyme catalyzing the peptide coupling (which may be the same or different as the enzyme used for the activation), whereby the N-terminal amino group of the optionally C-terminal protected amino acid or peptide is coupled to the activated C-terminal carboxy group, forming a peptide bond. The protecting group of the C-terminal protected amino acid or peptide, preferably is a t-alkyl, more preferably t-butyl, in particular in case the resultant peptide is to be elongated by one or more further amino acids or peptides. If desired, the C-terminal t-alkyl can be replaced by an activating group by transesterification, as disclosed herein, after which a further optionally C-terminal protected amino acid or peptide can be coupled. These reactions can be repeated as often as desired to obtain a peptide with a desired amino acid sequence.

Accordingly, the present invention also provides a process for the synthesis of peptides that allows peptide synthesis in the N→C terminal direction using a C-terminal t-alkyl, preferably t-butyl, protected amino acid or peptide. The method requires less reaction steps than a known method requiring a deprotection step and a separate activation step, since the C-terminus is effectively simultaneously deprotected and activated, in the presence of the enzyme, without requiring a chemical (non-enzymatic) deprotection process. Such conventional chemical process is further disadvantageous since it usually furthermore requires a purification, such as extensive extraction and dehydration procedures for the C-terminal carboxylic acid intermediate. Thus, the invention advantageously allows a completely enzymatic process for the synthesis of peptides in the N→C terminal direction, since also both the peptide chain elongation and the protection and deprotection of the N-terminal amino function may be performed completely enzymatically. Therefore, the process of the invention is more attractive than previously described processes, also making use of t-alkyl to protect carboxylic acid groups, for instance for reasons of simplifying the methodology and/or an environmental point of view.

With regard to the peptidic bond formation the same hydrolytic enzyme may be used, as long as it can catalyse peptidic bond formation. It is advantageous to use the same enzyme for the coupling as for transesterification, if such enzyme is capable of catalysing a peptidic bond formation, because thus a transesterification may be carried out to activate the C-terminal end of a peptide formed after the peptidic bond formation without first needing to isolate the protected peptide. This can simply be accomplished by changing solvents (a solvent switch) when changing from a first type of reaction to a second type of reaction. For instance, coupling of an activated amino-acid C-terminal ester with a C-terminal protected amino acid t-alkyl ester may take place in a tertiary alcohol, such as t-butyl alcohol. After coupling the solvent may be replaced by an aqueous liquid to facilitate hydrolysis of the protective group. The resultant free acid group may be activated after switching the solvent to the alcohol which upon esterification forms the activated C-terminal ester group. Preferably, the solvent wherein coupling has taken place is directly replaced by the alcohol which upon transesterification forms the activated C-terminal ester group.

However, a different enzyme may be used for peptidic bond formation. Suitable enzymes for catalysing peptidic bond formation are known to the skilled person and include proteolytic enzymes. Proteolytic enzymes (other names: proteases, peptidases, peptide hydrolases, E.C. 3.4) are enzymes that in nature hydrolyse peptidic bonds. These enzymes play an important role in various physiological processes, such as protein degradation, blood coagulation, apoptosis (cell death), and the immune system. These enzymes also serve as activators in the processing of peptide hormones and of enzyme precursors into the physiologically or catalytically active forms.

Proteases can be further divided into two subclasses, the exopeptidases, acting only near the terminus of a peptide, and the endopeptidases that act internally in a peptide.

The exopeptidases acting at the N-terminus of a peptide release a single amino acid (aminopeptidases E.C. 3.4.11) or dipeptides (dipeptidases, E.C. 3.4.13) or both dipeptides and tripeptides (dipeptidyl-peptidases or tripeptidyl-peptidases, E.C. 3.4.14). The peptidases acting at the C-terminus of a peptide are called carboxypeptidases and liberate a single amino acid (carboxypeptidases, E.C. 3.4.16-18) or a dipeptide (peptidyl-dipeptidases, E.C. 3.4.15). The carboxypeptidases are grouped according to their catalytic mechanism, e.g. serine-type carboxypeptidases (E.C. 3.4.16), metallocarboxypeptidases (E.C. 3.4.17), cysteine-type carboxypeptidases (E.C. 3.4.18) or cleave terminal amino acids that are substituted, cyclised, or that have isopeptide bonds (peptide bonds involving the side chain) (omega-peptidases, E.C. 3.4.19).

The endopeptidases (E.C. 3.4.21-25 and E.C. 3.4.99) can be divided into the following subclasses: serine endopeptidases (E.C. 3.4.21), cysteine endopeptidases (E.C. 3.4.22), aspartic endopeptidases (E.C. 3.4.23) and metalloendopeptidases (E.C. 3.4.24). E.C. 3.4.99 is for proteases with unknown catalytic mechanism.

In the literature also lipases (triacylglycerol hydrolase E.C. 3.1.1.1) have been reported to catalyse peptidic bond formation, e.g. lipase from porcine pancreas (PPL).

If desired, the optionally N-protected (oligo)peptide C-terminal t-alkyl-ester of the desired amino acid sequence may be deprotected on the C-terminus and/or on the N-terminus and/or—if at least one amino acid side chain protecting group is present—on at least one of the amino acid side chains, after which the protected or unprotected peptide may be recovered.

Deprotection of the N-terminal protecting group of the formed N-protected peptide C-terminal t-alkyl ester or N-protected C-terminal deprotected peptide may be performed by methods known to the person skilled in the art.

In an embodiment, the N-terminal protecting group is enzymatically removed.

Enzymes capable of introducing and removing an N-terminal protective group of a peptide are known to the skilled person and examples of such enzymes include penG acylases or peptide deformylase.

It is also possible to remove an N-terminal protective group chemically, e.g. by hydrogenation using $H_2$ in the presence of a Pd on carbon hydrogenation catalyst or by a suitable acid. Suitable conditions are known in the art.

The C-terminal t-alkyl ester function may in principle be removed with a strong acid, e.g. TFA, which may be troublesome (see above). Therefore, deprotection of the C-terminal t-alkyl ester function of the formed optionally N-protected peptide C-terminal t-alkyl ester may preferably be performed by using a hydrolytic enzyme, for instance a hydrolytic enzyme as identified above.

If an N-protected peptide C-terminal t-alkyl-ester without or with one or several amino acid side chain protecting groups, as obtained after the last peptide coupling step, is the desired end-product, this can be directly recovered, for example using an extraction or crystallization method known to the person skilled in the art. In case a partially protected peptide is the desired end product, one or more desired deprotection reaction(s) can be carried out and, optionally after a work-up procedure, the desired partially protected end product can be recovered.

When the completely deprotected peptide is the desired end-product, this peptide can be obtained by consecutive N-, C- and—if one or several amino acid side chain protecting groups are present after the last peptide coupling step— amino acid side chain deprotection steps. Procedures to finally recover the completely deprotected peptide can routinely be identified by a person skilled in the art. For instance one or more purification techniques selected from the group of extractions, chromatographic separations and crystallizations may be used.

Preferably, the peptide is recovered from the reaction mixture after the (final) coupling reaction.

The method of the invention is particularly suitable to synthesise a peptide by linear synthesis in the N→C terminal direction. In linear synthesis, the peptide is prepared by stepwise elongation, wherein step by step a single amino acid is added to the peptide chain until the peptide of the desired length and amino acid composition is formed (see for instance scheme 2, above). The peptides produced by the method of the invention preferably comprise a linear chain of 2-50 amino acids, in particular a linear chain of 2-20 amino acids, more in particular a linear chain of 2-10 amino acids.

If desired, two or more peptides prepared by linear syntheses may thereafter be coupled. Coupling may be accomplished by a chemical method, an enzymatic method or a combination thereof. For instance, chemical ligation, may be used, such as native chemical ligation.

Suitable chemical ligation methods are for instance described in "Dawson, P. E., Muir, T. W., Clark-Lewis, I. and Kent, S. B. H., Science, 1994, 266, p. 776", "Dawson, P. E. and Kent, S. B., Annu. Rev. Biochem., 2000, 69, p. 923, or Hacken, T. M., Griffin, J. H., Dawson, P. E., Proc. Natl. Acad. Sci. USA, 1999, 10068.

The invention is now illustrated by the following examples.

EXAMPLES

General

Unless stated otherwise, chemicals were obtained from commercial sources and used without further purification. $^1$H NMR spectra were recorded on a Bruker Avance 300 MHz NMR (300.1 MHz) spectrometer and chemical shifts are given in ppm (δ) relative to $CDCl_3$ (7.26 ppm) or $D_2O$ (4.79 ppm). Water contents were determined by Karl Fischer titration.

Thin layer chromatography (TLC) was performed on precoated silica gel 60 $F_{254}$ plates (Merck); spots were visualized using UV light, ninhydrin or $Cl_2$/TDM (N,N,N',N'-tetramethyl-4,4'-diaminodiphenylmethane).

Unless stated otherwise, 3 Å molsieves (8 to 12 mesh, Acros) were activated under reduced pressure at 200° C. and t-butanol ($^t$BuOH) was stored on these molsieves. $^t$BuOH was pre-heated to a liquid (45° C.) before use.

Column chromatography was carried out using silica gel, Merck grade 9385 60 Å. Analytical HPLC diagrams were recorded on an HP1090 Liquid Chromatograph, using a reversed-phase column (Inertsil ODS-3, C18, 5 µm, 150×4.6 mm internal diameter) at 40° C. UV detection was performed at 220 nm using a UV-VIS 204 Linear spectrometer. The gradient program was: 0-25 min linear gradient ramp from 5% to 98% eluent B and from 25.1-30 min to 5% eluent B (eluent A: 0.5 mL/L methane sulfonic acid (MSA) in $H_2O$, eluent B 0.5 mL/L MSA in acetonitrile). The flow was 1 mL/min from 0-25.1 min and 2 mL/min from 25.2-29.8 min, then back to 1 mL/min until stop at 30 min. Injection volumes were 20 µL.

Liquid chromatography electrospray ionization mass spectrometry was performed on an Agilent 1100 series system operating in a positive ionization mode, equipped with the same column under the same conditions as for analytical HPLC.

An Alcalase suspension in t-butanol was prepared as follows: 12.5 mL of Alcalase (Novozymes, Alcalase® 2.5 L, type DX, PLN04810) was precipitated with 10 mL of $^t$BuOH, vortexed for 5 min and centrifuged at 4500 rpm for 10 min. The supernatant was discarded and the previously described procedure was repeated twice. Finally, the pellet was resuspended in 10 mL of $^t$BuOH by vortexing for 5 min. An Alcalase suspension in t-amylalcohol ($^t$AmOH) was prepared likewise using $^t$AmOH instead of $^t$BuOH.

An Esperase, Everlase or Savinase suspension in t-butanol was prepared as follows: 10.0 mL of enzyme solution (Novozymes, Esperase® 8.0 L, PEN00103 or Everlase®, 16 L, Type EX, RCN00042 or Savinase®, 16 L, Type EX, PXN09325) was precipitated with 50 mL of $^t$BuOH, vortexed for 5 min and centrifuged at 4500 rpm for 10 min. The supernatant was discarded and the previously described procedure was repeated twice. Finally, the pellet was resuspended in 10 mL of $^t$BuOH by vortexing for 5 min.

An Alcalase-CLEA suspension was prepared as follows: 1 g crosslinked Alcalase-CLEA (CLEA-technologies, 650 AGEU/g, 3.5 wt % water), was suspended in 10 mL $^t$BuOH and crushed with a spatula. After filtration, the enzyme was resuspended in 10 mL $^t$BuOH prior to use.

A Polarzyme suspension was prepared as follows: 1 g of Polarzyme (Novozymes, Polarzyme®, 12 T, PGVG000905), was suspended in 10 mL $^t$BuOH. After filtration, the enzyme was resuspended in 10 mL $^t$BuOH prior to use.

Example 1

Preparation of N-Protected Amino Acid C-Terminal $^t$Bu and $^t$Am Esters from the Corresponding N-Protected Amino Acid Carboxylic Acids Several t-butyl ($^t$Bu) and t-amyl ($^t$Am) esters of amino acids were prepared using one of the protocols 1-3 as indicated below.

Protocol 1: Synthesis of Z-Protected Amino Acid C-Terminal $^t$Bu Esters from Z-Protected Amino Acids 3 mL of Alcalase suspension, prepared as described above, was added to 0.167 mmol of the Z-protected amino acid and 1 g of (non-activated) 3 Å molsieves. The mixture was shaken at 50° C. at 150 rpm for 24 h. Subsequently, 3 mL of MeOH was added and the solids were removed by filtration and washed with 10 mL ethyl acetate (EtOAc). The combined organic phase was centrifuged at 4500 rpm for 10 min and the supernatant was concentrated in vacuo.

The crude product was redissolved in 50 mL dichloromethane, washed with 25 mL saturated aqueous $NaHCO_3$ solution (3×), 25 mL saturated aqueous NaCl solution, dried ($Na_2SO_4$), concentrated in vacuo, and co-evaporated with 10 mL $CHCl_3$ (2×) and 10 mL toluene (2×).

Protocol 2: Synthesis of Z-Protected Amino Acid C-Terminal $^t$Bu Esters from Z-Protected Amino Acids 1 mL of Alcalase suspension, prepared as described above (but with $^t$BuOH stored on activated mol sieves), was added to 0.167 mmol of the Z-protected amino acid 0.5 g of 3 Å molsieves and diluted with 2 mL $^t$BuOH. This mixture was shaken at 50° C. at 150 rpm for 24 h.

Protocol 3: Synthesis of N-Protected-Phe $^t$Bu Esters from N-Protected-Phe Using Alcalase-CLEA 3 mL of Alcalase-CLEA suspension, prepared as described above, was added to 0.167 mmol X-Phe-OH and 0.1 g activated 3 Å molsieves (wherein X stands for an N-terminal protective group). The mixture was shaken at 50° C. at 150 rpm for 24 h.

After removing the solids by filtration, the filtrate was evaporated in vacuo and the crude product was redissolved in 20 mL EtOAc, washed with 10 mL saturated aqueous NaHCO$_3$ solution, 10 mL brine, dried (Na$_2$SO$_4$), concentrated in vacuo and co-evaporated with 10 mL CHCl$_3$ (2×).

Z-Phe-O$^t$Bu

Z-Phe-O$^t$Bu was prepared according to protocol 2. HPLC analysis indicated a conversion to the $^t$Bu ester of 88% after 24 h. $^1$H-NMR (CDCl$_3$, 300 MHz): δ 7.28-7.05 (m, 10H), 5.22 (d, 1H, J=7.9 Hz), 5.01 (s, 2H), 4.45 (m, 1H), 2.98 (d, 2H, J=6.0 Hz), 1.30 (s, 9H).

Z-Phe-O$^t$Bu

Z-Phe-O$^t$Bu was prepared according to protocol 1 with the exception that an Esperase suspension was used instead of an Alcalase suspension. HPLC analysis indicated a conversion to the $^t$Bu-ester of 38% after 24 h.

Z-Phe-O$^t$Bu

Z-Phe-O$^t$Bu was prepared according to protocol 1 with the exception that a Savinase suspension was used instead of an Alcalase suspension. HPLC analysis indicated a conversion to the $^t$Bu-ester of 43% after 24 h.

Z-Phe-O$^t$Bu

Z-Phe-O$^t$Bu was prepared according to protocol 1 with the exception that an Everlase suspension was used instead of an Alcalase suspension. HPLC analysis indicated a conversion to the $^t$Bu-ester of 24% after 24 h.

Z-Phe-$^t$Bu

Z-Phe-$^t$Bu was prepared according to protocol 1 with the exception that a Polarzyme suspension was used instead of an Alcalase suspension. HPLC analysis indicated a conversion to the $^t$Bu-ester of 17% after 24 h.

Z-Phe-O$^t$Am

Z-Phe-O$^t$Am was prepared according to protocol 2 with the exception that $^t$AmOH was used instead of $^t$BuOH. HPLC analysis indicated a conversion to the $^t$Am-ester of 93% after 24 h. $^1$H-NMR (CDCl$_3$, 300 MHz): δ 7.30-7.01 (m, 10H), 5.20 (d, 1H, J=7.8 Hz), 5.00 (s, 2H), 4.46 (m, 1H), 3.04-2.92 (m, 2H) 1.72-1.49 (m, 2H), 1.31 (s, 3H), 1.28 (s, 3H), 0.74 (t, 3H, J=7.5 Hz)

Z,Z-Lys-O$^t$Bu

Z,Z-Lys-O$^t$Bu was prepared according to protocol 1. HPLC indicated a conversion to the $^t$Bu ester of >90% after 24 h. $^1$H-NMR (CDCl$_3$, 300 MHz): δ 7.25-7.16 (m, 10H), 5.31 (d, 1H, J=5.6 Hz), 5.01 (s, 4H), 4.81 (s, 1H), 4.15 (d, 1H, J=5.1 Hz), 3.08 (m, 2H), 1.72 (m, 2H), 1.57 (m, 2H), 1.43 (m, 2H), 1.37 (s, 9H).

Z-Leu-O$^t$Bu

Z-Leu-O$^t$Bu was prepared according to protocol 1. HPLC indicated a conversion to the $^t$Bu ester of >90% after 24 h. $^1$H-NMR (CDCl$_3$, 300 MHz): δ 7.27-7.19 (m, 5H), 5.10 (d, 1H, J=8.1 Hz), 5.03 (s, 2H), 4.19 (m, 1H), 1.60 (m, 2H), 1.45 (m, 1H), 1.38 (s, 9H), 0.88 (m, 6H).

Z-Ala-O$^t$Bu

Z-Ala-O$^t$Bu was prepared according to protocol 1. HPLC indicated a conversion to the $^t$Bu ester of >90% after 24 h. $^1$H-NMR (CDCl$_3$, 300 MHz): δ 7.31-7.18 (m, 5H), 5.29 (d, 1H, J=6.0 Hz), 5.03 (s, 2H), 4.18 (t, 1H, J=7.2 Hz), 1.38 (s, 9H), 1.29 (d, 3H, J=7.1 Hz).

Z-Met-O$^t$Bu

Z-Met-O$^t$Bu was prepared according to protocol 1. HPLC indicated a conversion to the $^t$Bu ester of >90% after 24 h. $^1$H-NMR (CDCl$_3$, 300 MHz): δ 7.30-7.19 (m, 5H), 5.33 (d, 1H, J=7.60 Hz), 5.04 (s, 2H), 4.29 (m, 1H), 2.45 (m, 2H), 2.01 (s, 3H), 1.87 (m, 2H), 1.39 (s, 9H).

Z-Ser-O$^t$Bu

Z-Ser-O$^t$Bu was prepared according to protocol 1. HPLC indicated a conversion to the $^t$Bu ester of 82% after 24 h. Additional column chromatography (n-heptane/EtOAc, 1/1) was needed for final purification. $^1$H-NMR (CDCl$_3$, 300 MHz): δ 7.30-7.19 (m, 5H), 5.57 (s, 1H), 5.06 (s, 2H), 4.25 (m, 1H), 3.86 (m, 2H), 2.09 (s, 1H), 1.41 (s, 9H).

Z-DOPA-O$^t$Bu 10 mL of Alcalase solution, as prepared above, was added to 3 g (9.1 mmol) Z-DOPA-OH and 10 g of 3 Å molsieves and diluted with 20 mL $^t$BuOH. This mixture was shaken at 50° C. with 150 rpm and analyzed by HPLC using commercially available Z-DOPA-O$^t$Bu as reference showing a conversion to the $^t$Bu ester of >90% after 24 h.

For-Phe-O$^t$Bu

For-Phe-O$^t$Bu was prepared according to protocol 3. HPLC indicated a conversion to the $^t$Bu ester of 98% after 24 h. $^1$H-NMR (CDCl$_3$, 300 MHz): δ 8.04 (s, 1H), 7.22-7.07 (m, 5H), 4.99 (d, 1H, 1H, J=7.3 Hz), 4.75 (m, 1H), 3.02 (d, 2H, J=5.6 Hz), 1.33 (s, 9H).

Boc-Phe-O$^t$Bu

Boc-Phe-O$^t$Bu was prepared according to protocol 3. HPLC indicated a conversion to the $^t$Bu ester of 98% after 24 h. $^1$H-NMR (CDCl$_3$, 300 MHz): δ 7.28-7.16 (m, 5H), 4.99 (d, 1H, J=7.8 Hz), 4.45 (m, 1H), 3.04 (d, 2H, J=6.0 Hz), 1.42 (s, 9H), 1.40 (s, 9H).

PhAc-Phe-O$^t$Bu

PhAc-Phe-O$^t$Bu was prepared according to protocol 3. HPLC indicated a conversion to the $^t$Bu ester of 94% after 24 h. $^1$H-NMR (CDCl$_3$, 300 MHz): δ 7.29-6.87 (m, 10H), 5.77 (d, 1H, J=7.8 Hz), 4.66 (m, 1H) 3.53 (s, 2H), 3.45 (d, 2H, J=6.1), 1.30 (s, 9H).

Example 2

Transesterification of Z-Phe-O$^t$Bu to the Corresponding Methyl (Me), Ethyl (Et) and Benzyl (Bn) Esters Transesterification of Z-Phe-O$^t$Bu to Z-Phe-OMe

Alcalase was prepared as described in the general section except that the pellet was not resuspended in $^t$BuOH but in 10 mL CH$_3$CN:MeOH 85:15 v/v or $^t$BuOH:MeOH 9:1 v/v. 3 mL of this suspension was added to 50 mg Z-Phe-O$^t$Bu and 0.5 g of 3 Å molsieves.

The mixture was shaken at 50° C. with 150 rpm and analyzed by HPLC using the corresponding chemically synthesized reference compound.

Figure 1A:
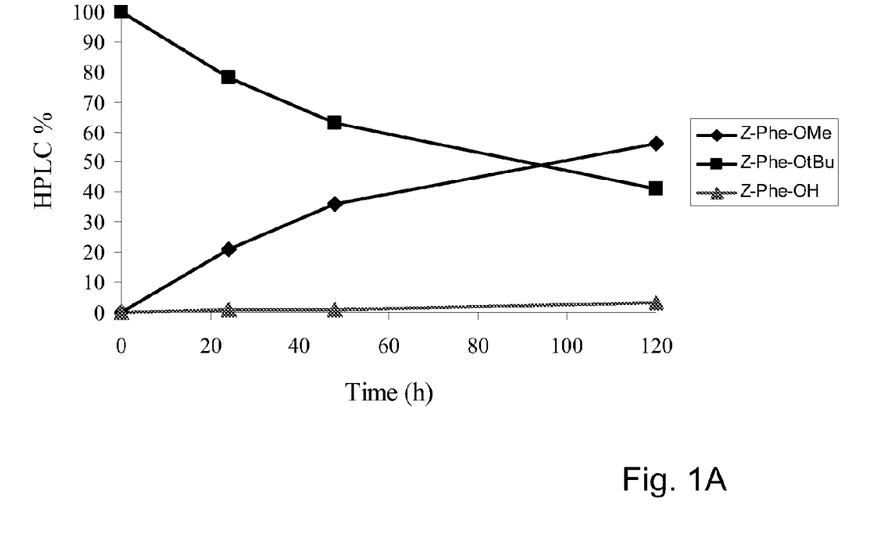
FIGS. 1A and 1B show the conversion as a function of reaction time of a transesterification of Z-Phe-O$^t$Bu to Z-Phe-OMe by Alcalase® using: (A) CH$_3$CN:MeOH 85:15 v/v; (B) $^t$BuOH:MeOH 9:1 v/v.
Figure 1B:
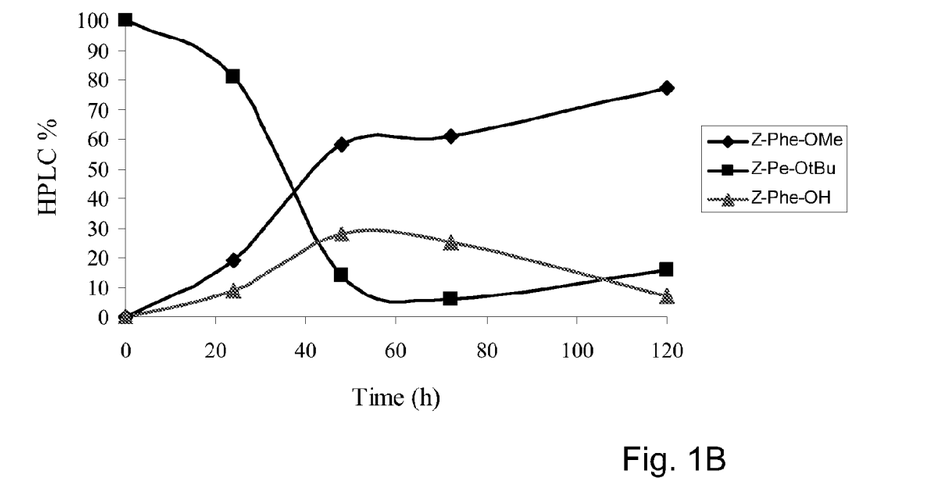

The results are shown in FIGS. 1A and 1B. Herein it is shown that a higher yield and faster conversion could be obtained using $^t$BuOH as the co-solvent (77% conversion after 120 h) than with acetonitrile.

Transesterification of Z-Phe-O$^t$Bu to Z-Phe-OEt

Alcalase was prepared as described in the general section except that the pellet was not resuspended in $^t$BuOH but in 10 mL ethanol (EtOH). 3 mL of this suspension was added to 50 mg Z-Phe-O$^t$Bu (no molsieves were used). The mixture was shaken at 50° C. with 150 rpm and analyzed by HPLC using the corresponding chemically synthesized reference compound.

Figure 2:
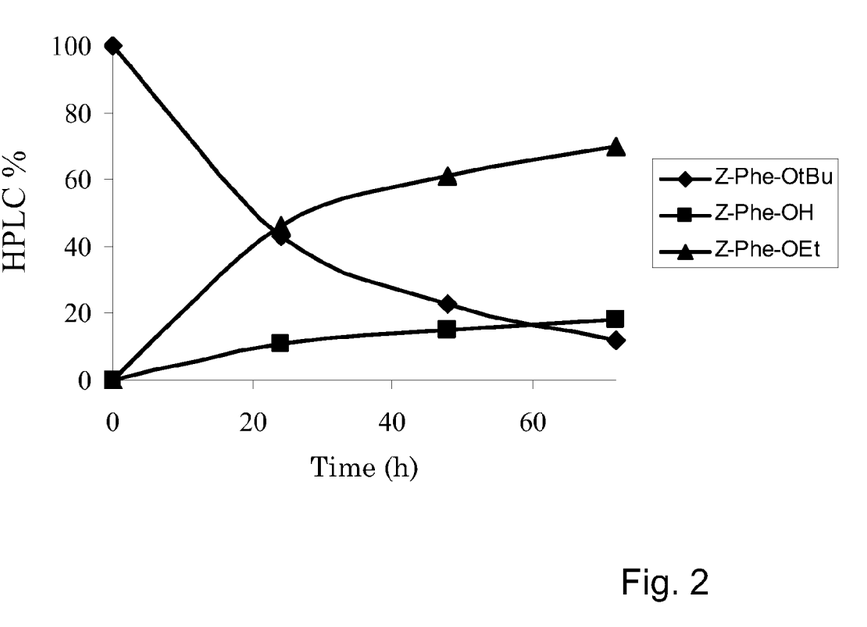
FIG. 2 shows the conversion as a function of reaction time of a transesterification of Z-Phe-O$^t$Bu to Z-Phe-OEt by Alcalase®.

The results are shown in FIG. 2. After 96 h reaction time 73% of Z-Phe-O$^t$Bu had been converted to the corresponding ethyl ester.

Transesterification of Z-Phe-O$^t$Bu to Z-Phe-OBn

Alcalase was prepared as described in the general section except that the pellet was not resuspended in $^t$BuOH but in 10 mL benzyl alcohol (BnOH). 3 mL of this suspension was added to 50 mg Z-Phe-O$^t$Bu and 0.5 g of 3 Å molsieves. The mixture was shaken at 50° C. with 150 rpm and analyzed by HPLC using the corresponding chemically synthesized reference compound.

Figure 3:
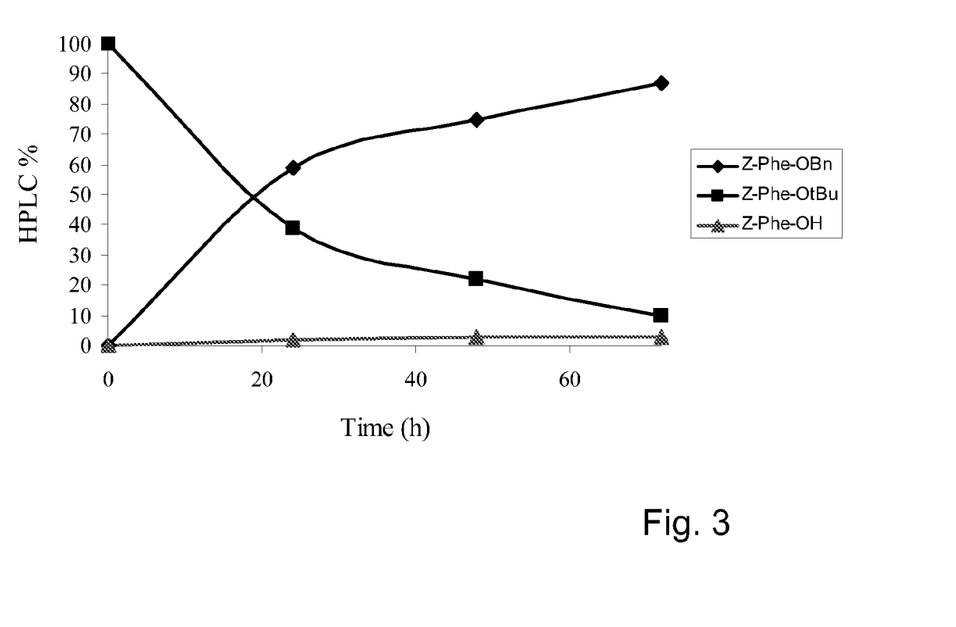
FIG. 3 shows the conversion as a function of reaction time of a transesterification of Z-Phe-O$^t$Bu to Z-Phe-OBn by Alcalase®.

The results are shown in FIG. 3. The reaction rate was considerably higher (87% conversion in 72 h) compared to the transesterification reactions to the corresponding Me and Et esters (see above).

Example 3

Transesterification Reactions on Dipeptide Level (Z-Phe-Leu)

In specific cases, when the substrate is a peptide, and especially when the hydrolytic enzyme is a peptidase, it would be expected that during transesterification or activation peptide bond hydrolysis would simultaneously take place. Whether this occurred. Therefore the experiments described below were performed to check whether this detrimental effect occurred in a method of the invention.

As model substrates Z-Phe-Leu derivative were used in combination with subtilisin Carlsberg, since this peptidase is able to catalyse synthesis of these dipeptide derivatives by peptidic bond formation, so these peptides are also good model substrates to observe any peptide bond cleavage. First, all reference compounds were synthesized by solution-phase chemical peptide synthesis.

Figure 4:
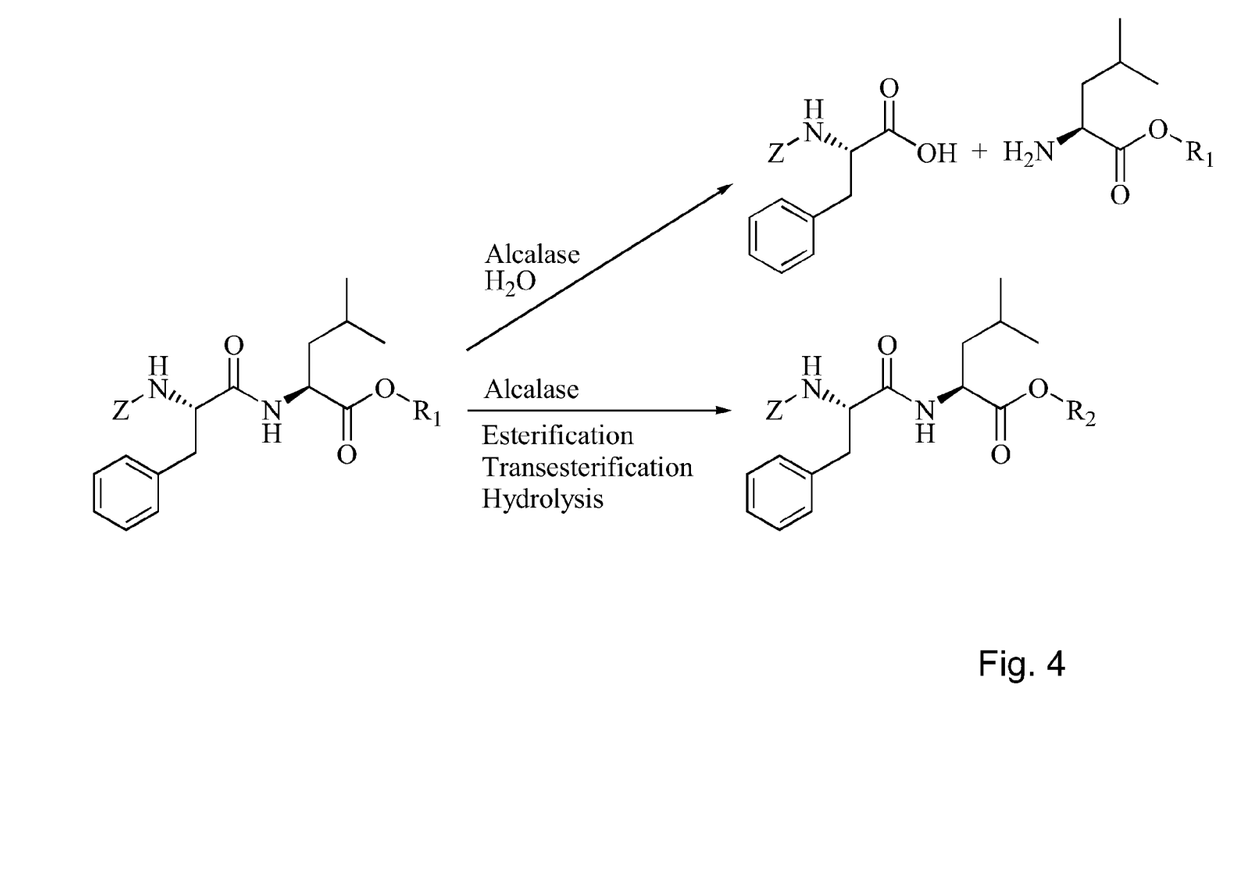
FIG. 4 shows a reaction scheme illustrating esterification, transesterification and hydrolysis of a model dipeptide by Alcalase® respectively a peptidic bond cleavage.

Reaction paths are illustrated in FIG. 4, wherein $R_1$, $R_2$ are H, an activating group or a t-alkyl, depending upon which of the reactions indicated in the figure is carried out, for instance $R_1$=H and $R_2$ is an activating group or t-butyl when transesterifying; $R_1$=t-butyl and $R_2$ is an activating group when esterifying; $R_1$ is an activating group or t-butyl and $R_2$ is hydrogen when hydrolysing the $R_1$ group.

Z-Phe-Leu-O$^t$Bu (Chemical Synthesis of Reference Compound)

500 mg (1.7 mmol) Z-Phe-OH was dissolved in 10 mL of CH$_2$Cl$_2$. Subsequently, 415 mg N-(3-dimethylaminopropyl)-N'-ethylcarbodiimide.HCl (EDCl, 2.2 mmol, 1.3 eq), 250 mg 7-aza-N-hydroxybenzatriazole (HOAt, 1.8 mmol, 1.1 eq), 478 μL triethylamine (TEA, 1.8 mmol, 1.1 eq) and 344 mg H-Leu-O$^t$Bu (1.8 mmol, 1.1 eq) were added. The reaction mixture was stirred at ambient temperature for 20 h. Subsequently, 20 mL EtOAc was added and the organic mixture was washed with 15 mL saturated aqueous Na$_2$CO$_3$ (2×), 15 mL saturated aqueous NaHCO$_3$ (2×), 15 mL brine, dried (Na$_2$SO$_4$), concentrated in vacuo and co-evaporated with 10 mL toluene (2×) to yield 765 mg (98%) Z-Phe-Leu-O$^t$Bu. $^1$H-NMR (CDCl$_3$, 300 MHz): δ 7.09-7.31 (m, 10H), 6.13 (d, 1H, J=8.0 Hz), 5.23 (d, 1H, J=6.8), 5.01 (s, 2H), 4.36 (m, 2H), 3.02 (m, 2H), 1.45 (m, 3H), 1.37 (s, 9H), 0.84 (m, 6H).

Z-Phe-Leu-OH (Chemical Synthesis of Reference Compound)

100 mg Z-Phe-Leu-O$^t$Bu was added to 5 mL CF$_3$COOH to which a drop of water had been added. The mixture was stirred for 2 h at ambient temperature, concentrated in vacuo and co-evaporated with 10 mL toluene (2×) to obtain Z-Phe-Leu-OH in quantitative yield. $^1$H-NMR (CDCl$_3$, 300 MHz): δ 7.31-7.04 (m, 10H), 6.82 (d, 1H, J=6.6 Hz), 5.79 (d, 1H, J=7.3 Hz), 4.93 (s, 2H), 4.44 (m, 2H), 2.94 (m, 2H), 1.51 (m, 3H), 0.77 (m, 6H).

Z-Phe-Leu-OMe (Chemical Synthesis of Reference Compound)

364 mg (2.0 mmol) HCl.H-Leu-OMe was dissolved in 20 mL CHCl$_3$ and 699 μL diisopropylethylamine (DIPEA, 4 mmol, 2 eq). This solution was added to a solution (0° C.) of 599 mg (2 mmol, 1 eq) Z-Phe-OH, 403 mg EDCl (2.1 mmol, 1.05 eq) and 300 mg HOAt (2.2 mmol, 1.2 eq) in 20 mL CHCl$_3$. The mixture was stirred at ambient temperature for 16 h. The solution was concentrated in vacuo, the residue redissolved in 20 mL EtOAc, washed with 15 mL aqueous HCl (pH=3), 15 mL brine, 15 mL saturated aqueous $Na_2CO_3$, 15 mL brine, dried ($Na_2SO_4$), and concentrated in vacuo.

Additional column chromatography (EtOAc/n-heptane, 1/1) yielded 625 mg (80%) of Z-Phe-Leu-OMe. $^1$H-NMR ($CDCl_3$, 300 MHz): δ 7.32-7.11 (m, 10H), 6.06 (d, 1H, J=8.0 Hz), 5.22 (d, 1H, J=11.7 Hz), 5.02 (s, 2H), 4.50 (m, 1H), 4.36 (m, 1H), 3.62 (s, 3H) 3.04 (m, 2H), 1.47 (m, 3H), 0.80 (m, 6H).

Z-Phe-Leu-OBn (Chemical Synthesis of Reference Compound)

1.57 g (4 mmol) p-tosylate.H-Leu-OBn was dissolved in 20 mL $CH_2Cl_2$ and 1.4 mL DIPEA, (8 mmol, 2 eq). This solution was added to a solution (0° C.) of 1.20 g (2 mmol, 1 eq) Z-Phe-OH, 805 mg EDCl (4.2 mmol, 1.05 eq) and 599 mg HOAt (4.4 mmol, 1.2 eq) in 20 mL $CH_2Cl_2$. The mixture was stirred at ambient temperature for 16 h. The solution was concentrated in vacuo, the residue redissolved in 40 mL EtOAc, washed with 25 mL aqueous HCl (pH=3, 2×), 25 mL brine, 25 mL saturated aqueous $Na_2CO_3$ (2×), 25 mL brine, dried ($Na_2SO_4$), and concentrated in vacuo.

Additional column chromatography (EtOAc/n-heptane, 1/1) yielded 2.0 g (100%) of Z-Phe-Leu-OBn. $^1$H-NMR ($CDCl_3$, 300 MHz): δ 7.42-7.17 (m, 10H), 6.15 (d, 1H, J=8.1 Hz), 5.29 (d, 1H, J=4.3), 5.14 (s, 2H), 5.09 (s, 2H), 4.61 (m, 1H), 4.41 (m, 1H), 3.07 (m, 2H), 1.57 (m, 1H) 1.46 (m, 2H), 0.87 (m, 6H).

Hydrolysis of Z-Phe-Leu-O$^t$Bu to Z-Phe-Leu-OH 300 mg Alcalase-CLEA was added to a mixture of 1.5 mL 50 mM aqueous Tris/HCl buffer (pH=8), 1.5 mL $^t$BuOH and 100 mg Z-Phe-Leu-O$^t$Bu. The reaction mixture was shaken at 37° C. with 100 rpm for 16 h and analyzed by HPLC with the corresponding reference compounds (prepared as described above).

HPLC analysis showed that 98% of the $^t$Bu ester had been hydrolysed without detectable peptidic bond cleavage.

Esterification of Z-Phe-Leu-OH to Z-Phe-Leu-OMe

Alcalase-CLEA was prepared as described earlier except that the enzyme was resuspended in 10 mL 5 vol % MeOH in MTBE. 3 mL of this suspension was added to 100 mg Z-Phe-Leu-OH and 0.1 g of 3 Å molsieves. The mixture was shaken at 37° C. with 100 rpm for 16 h and analyzed by HPLC with the corresponding reference compound (prepared as described above).

HPLC analysis showed that the esterification was essentially complete (98% Me ester) without detectable peptidic bond cleavage.

Transesterification of Z-Phe-Leu-OMe to Z-Phe-Leu-OBn

Alcalase-CLEA was prepared as described earlier except that the enzyme was resuspended in 10 mL BnOH. 3 mL of this suspension was added to 100 mg Z-Phe-Leu-OMe and 0.1 g of 3 Å molsieves. The mixture was shaken at 37° C. with 100 rpm for 24 h and analyzed by HPLC with the corresponding reference compounds (prepared as described above).

HPLC analysis showed that the conversion to the Bn ester was 84% without detectable peptidic bond cleavage Transesterification of Z-Phe-Leu-O$^t$Bu to Z-Phe-Leu-OMe Alcalase-CLEA was prepared as described earlier except that the enzyme was resuspended in 10 mL 5 vol % MeOH in MTBE. 3 mL of this suspension was added to 100 mg Z-Phe-Leu-O$^t$Bu and 0.1 g of 3 Å molsieves. The mixture was shaken at 37° C. with 100 rpm for 24 h and analyzed by HPLC with the corresponding reference compounds (prepared as described above).

HPLC analysis showed that Z-Phe-Leu-O$^t$Bu was converted to Z-Phe-Leu-OMe (81%) without peptidic bond cleavage.

Example 4

Esterification with Azeotropic Removal of Water and Alcohols

Z-Phe-OH was converted to Z-Phe-O$^t$Bu whilst removing water by carrying out the reaction under a reduced pressure (to accomplish azeotropic water removal).

Thus, the reaction was performed in a round-bottomed flask with 7.5 g Alcalase-CLEA (washed once with $^t$BuOH), 75 mL $^t$BuOH and 1.25 g of Z-Phe-OH. The mixture was stirred at 50° C. while vacuum (until boiling, P≈600 mbar) was applied every other h (e.g. between t=20-21 h and 22-23 h, FIG. 5B). The evaporated solvents were collected in a gas trap.

Figure 5A:
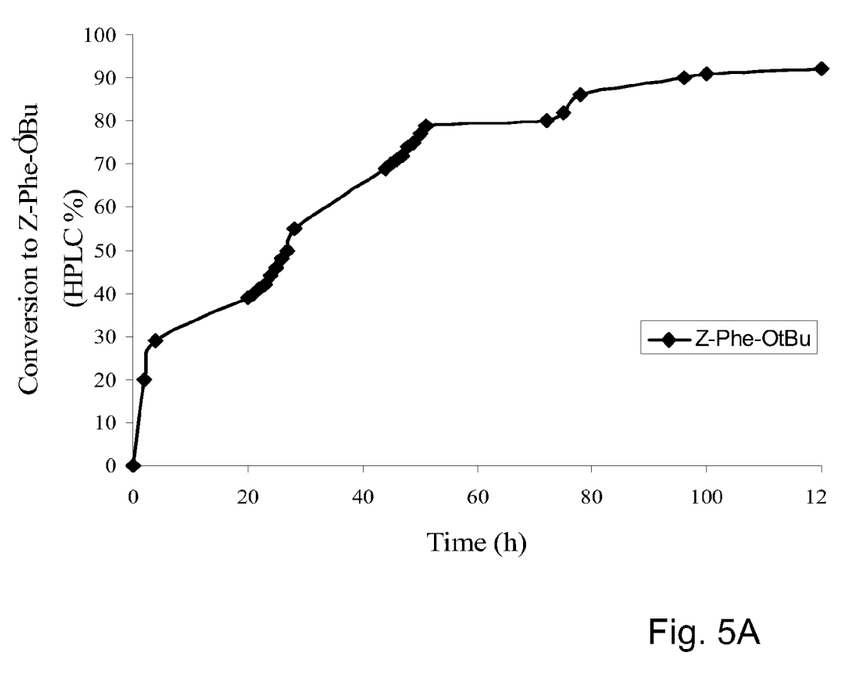
FIGS. 5A and 5B show A) the conversion of Z-Phe-OH to Z-Phe-O$^t$Bu by Alcalase®, with azeotropic water removal; and B) the corresponding water content of the reaction in time.
Figure 5B:
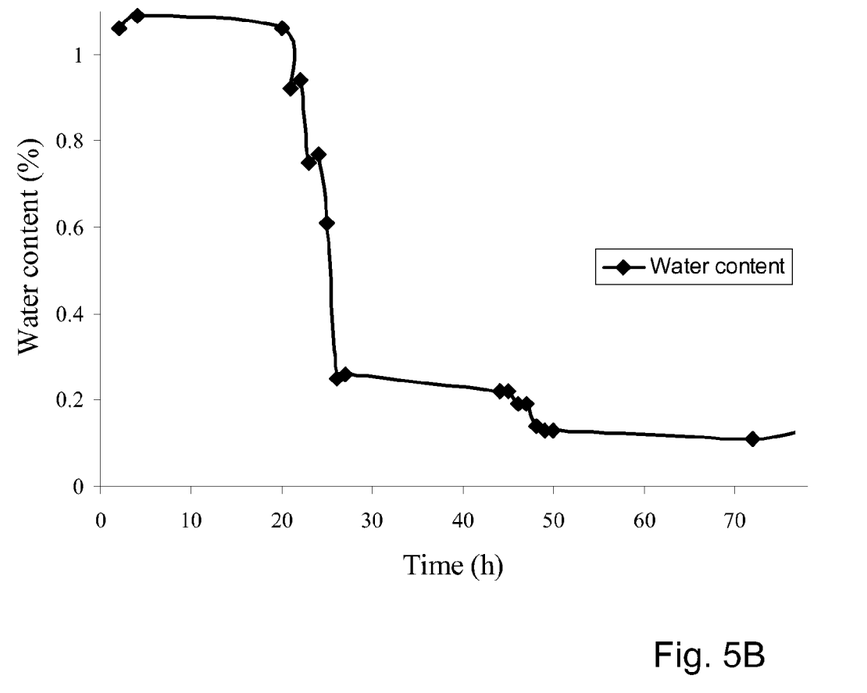

Every hour, a sample (2 mL) was taken to monitor the progress of the esterification reaction by HPLC (FIG. 5A) and to determine the water content of the reaction mixture (FIG. 5B). After 1 h of vacuum, the reaction mixture was stirred for 1 h (at 50° C.) under nitrogen to investigate whether the water content would raise due to product formation (e.g. between t=21-22 h and 23-24 h, FIG. 5B). Because the reaction volume decreased due to evaporation and sampling, fresh $^t$BuOH (to a volume of 50 mL) was added when needed (e.g. between t=24-25 h, FIG. 5B). Evidently, there was a strong correlation between water content and vacuum (a drop in water content when vacuum was applied, FIG. 5B) and also between water content and product yield (sharp yield rise after decrease of water content, FIG. 5A).

Thus, application of vacuum proved to be a successful method for water removal and comparable yields of Z-Phe-O$^t$Bu ester were obtained (92%, FIG. 5A) as with 3 Å molsieves (96%).

Example 5

Enzyme Recycling 1 g Alcalase-CLEA, washed once with 30 mL $^t$BuOH, was added to 10 mL $^t$BuOH and 150 mg Z-Phe-OH. The mixture was shaken at 50° C. with 150 rpm for 24 h. HPLC indicated that the conversion of Z-Phe to Z-Phe-O$^t$Bu was 60%. Subsequently, the reaction mixture was filtered and the Alcalase-CLEA resuspended in 10 mL $^t$BuOH and 150 mg Z-Phe-OH. The mixture was shaken at 50° C. with 150 rpm for 24 h. HPLC indicated that the conversion of Z-Phe to Z-Phe-O$^t$Bu was 77%. This procedure was repeated twice (77% and 76% esterification to Z-Phe-O$^t$Bu respectively). After filtration, the enzyme was stored at 4° C. for 2 days, followed by resuspension in 10 mL $^t$BuOH and 150 mg Z-Phe-OH. The mixture was shaken at 50° C. with 150 rpm and after 24 h HPLC indicated that the conversion of Z-Phe to Z-Phe-O$^t$Bu was 75%. This proves that there was hardly any deactivation of the enzyme during recycling.

Example 6

Synthesis of a Tripeptide Using C-Terminal t-Butyl Ester Transesterification

Z-Phe-Leu-O$^t$Bu

10 mL of Alcalase solution (Novozymes, Alcalase 2.5 L, type DX) was suspended in anhydrous tert-BuOH (25 mL) by agitation. The resulting mixture was centrifuged and the solvent was removed by decantation. The procedure was repeated twice using tert-BuOH and twice using MTBE. Finally, the enzyme was suspended in MTBE (30 mL) and 6 mL of the resulting mixture was added to a mixture of Z-Phe-OMe (94 mg, 0.3 mmol) and H-Leu-O$^t$Bu (169 mg, 0.9 mmol).

The reaction mixture was stirred at 50° C. for three days until analytical HPLC analysis indicated that conversion to the dipeptide was complete. The enzyme was removed by filtration and the solvent was removed in vacuo. The residue was redissolved in EtOAc (20 mL) and subsequently washed with aqueous HCl (10 mL, pH=3, 2×), brine (10 mL), saturated aqueous NaHCO$_3$ (10 mL, 2×) and brine (10 mL), dried (Na$_2$SO$_4$) and concentrated.

From the crude product (115 mg, 82%), Z-Phe-Leu-O$^t$Bu (55 mg, 39%) was isolated by flash column chromatography (eluent: EtOAc/n-heptane 1:1 v/v) as a clear oil that solidified upon standing.

R$_f$=0.53 (eluent: EtOAc/n-heptane 1:1 v/v), R$_t$=24.17 min, $^1$H-NMR (CDCl$_3$) δ 7.30-7.10 (m, 10H), 6.11 (d, J=8.03 Hz, 1H), 5.21 (br s, 1H), 5.01 (s, 2H), 4.36 (m, 2H), 3.02 (m, 2H), 1.50 (m, 3H), 1.37 (s, 9H), 0.82 (dd, J=2.23 Hz, J=3.82 Hz, 6H).

Z-Phe-Leu-OMe

750 mg of Alcalase-CLEA was washed once with $^t$BuOH (25 mL) before it was added to a solution of Z-Phe-Leu-O$^t$Bu (30 mg) in MTBE/MeOH (6 mL, 97:3 v/v). The reaction mixture was shaken at 50° C. for 16 h until HPLC analysis indicated >97% conversion to the methyl ester. The enzyme was removed by filtration and the solvents were removed by concentration in vacuo.

R$_f$=0.39 (eluent: EtOAc/n-heptane 1:1 v/v), R$_t$=20.67 min, $^1$H-NMR (CDCl$_3$) δ 7.32-7.11 (m, 10H), 6.08 (d, J=8.03 Hz, 1H), 5.22 (br s, 1H), 5.02 (s, 2H), 4.49 (m, 1H), 4.36 (m, 1H), 3.62 (s, 3H), 3.01 (m, 2H), 1.47 (m, 3H), 0.81 (m, 6H).

Z-Phe-Leu-Gly-O$^t$Bu

10 mL of Alcalase solution (Novozymes, Alcalase 2.5 L, type DX) was suspended in anhydrous $^t$BuOH (25 mL) by agitation. The resulting mixture was centrifuged and the solvent removed by decantation. The procedure was repeated twice using $^t$BuOH and twice using MTBE. Finally, the enzyme was suspended in MTBE (30 mL) and 6 mL of the resulting mixture was added to a mixture of Z-Phe-Leu-OMe (128 mg, 0.3 mmol) and H-Gly-O$^t$Bu (118 mg, 0.9 mmol).

The reaction mixture was stirred at 50° C. After two days HPLC analysis indicated approx. 50% conversion to the tripeptide and the reaction was stopped. The enzyme was removed by filtration and the solution concentrated in vacuo. The product (43 mg, 28%) was isolated by flash column chromatography (eluent: gradient EtOAc/n-heptane 1:3 v/v→EtOAc/n-heptane 1:1 v/v) as a clear oil that solidified upon standing. R$_f$=0.28 (eluent: EtOAc/n-heptane 1:1 v/v), R$_t$=22.02 min, $^1$H-NMR (CDCl$_3$) δ 7.30-7.10 (m, 10H), 6.46 (br s, 1H), 6.32 (d, J=8.03 Hz, 1H), 5.29 (d, J=7.27 Hz, 1H), 5.00 (s, 2H), 4.39 (m, 2H), 3.77 (m, 2H), 3.01 (m, 2H), 1.61 (m, 3H), 1.39 (s, 9H), 0.83 (m, 6H).

TFA.H-Phe-Leu-Gly-OH

First, the Z-protecting group was removed by treating a solution of Z-Phe-Leu-Gly-O$^t$Bu (59 mg, 0.11 mmol) in THF/H$_2$O (4 mL, 1:1 v/v) with hydrogen gas (1 bar) in the presence of palladium (10% on activated carbon). The reaction mixture was stirred at ambient temperature for 16 h and the catalyst was removed by filtration over Decalite. The resulting solution was concentrated in vacuo and the residue was co-evaporated with subsequently toluene and chloroform. Complete removal of the Z-protecting group was confirmed by HPLC analysis.

Subsequently, the residue was treated with TFA/CH$_2$Cl$_2$ (6 mL, 1:1 v/v) at ambient temperature for 3 h to remove the $^t$Bu ester. The mixture was concentrated in vacuo and the residue was subsequently coevaporated with chloroform and titurated with Et$_2$O to afford the tripeptide product (41 mg, 80%) as a white solid.

The identity of TFA.H-Phe-Leu-Gly-OH was confirmed by HPLC-MS and $^1$H-NMR spectroscopy. R$_t$=6.39 min, ESMS calcd. for C$_{17}$H$_{25}$N$_3$O$_4$ 335.18, found 336 [M+H]$^+$.

¹H-NMR (D₂O) δ 7.35-7.20 (m, 5H), 4.34 (m, 1H), 4.20 (m, 1H), 3.86 (m, 2H), 3.15 (m, 2H), 1.53 (m, 3H), 0.82 (m, 6H).

Example 7

Esterification of N-Protected Amino Acid with Subtilisin-A

Lyophilized Subtilisin-A (1 g, Novozymes) was dissolved in 10 mL Tris/HCl buffer (pH=8) and precipitated with 20 mL ᵗBuOH. After centrifugation (10 min, 4500 rpm) the supernatant was discarded and the pellet resuspended in 20 mL ᵗBuOH. This procedure was repeated twice. After final decantation, 200 mg of the pellet was resuspended in 3 mL ᵗBuOH and 50 mg Z-Phe-OH and 100 mg 3 Å molsieves were added. This mixture was shaken at 50° C. at 150 rpm. HPLC analysis after 16 h indicated a conversion to the ᵗBu ester of >60%.

The invention claimed is:

1. A method for preparing a peptide comprising coupling an activated, N-protected, amino acid C-terminal ester or an activated, optionally N-protected, peptide C-terminal ester, the coupling comprising
activating a t-alkyl C-terminal ester of a first N-protected amino acid or a t-alkyl C-terminal ester of a first, optionally N-protected, peptide by transesterification with an activating alcohol, the activation being catalysed by a peptidase (E.C. 3.4), thereby forming a second N-protected amino acid C-terminal ester or a second, optionally N-protected, peptide C-terminal ester; and wherein the transesterification takes place in a liquid phase comprising the activating alcohol, which liquid phase comprises less than 2 wt. % water, based on the total weight of the liquid phase; and
coupling the second ester with an, optionally C-terminal protected, amino acid or an, optionally C-terminal protected, peptide forming a peptidic bond, the coupling being catalysed by an enzyme catalysing peptidic bond formation, which enzyme may be the same as or different from the enzyme used for catalysing the transesterification.

2. The method according to claim 1, wherein the C-terminal t-alkyl ester of the amino acid or peptide is selected from the group of t-butyl esters, t-pentyl esters and t-hexyl esters.

3. The method according to claim 1, wherein consecutively one or more further activation steps and coupling steps are carried out until a peptide of a desired amino acid sequence is obtained.

4. The method according to claim 1, wherein consecutively one or more further transesterification steps and coupling steps are carried out until a peptide of a desired amino acid sequence is obtained.

5. The method according to claim 1, wherein the liquid phase comprises 1 wt. % water or less, based on the total weight of the liquid phase.

6. The method according to claim 1, wherein the activating alcohol is selected from the group of optionally substituted n-alkyl alcohols, optionally substituted aralkyl alcohols and optionally substituted aryl alcohols.

7. The method for preparing an N-protected amino acid C-erminal ester or an, optionally N-protected, peptide C-terminal ester, comprising transesterifying a C-terminal t-alkyl ester of the N-protected amino acid or a C-terminal t-alkyl ester of the optionally N-protected peptide with an alcohol—other than the t-alkyl alcohol corresponding to the t-alkyl group of the first ester—in the presence of a peptidase (E.C. 3.4), and wherein the transesterification is carried out in a liquid phase comprising the alcohol and which liquid phase comprises 2 wt. % water or less, based on the total weight of the liquid phase.

8. The method according to claim 7, wherein the transesterification is carried out in a liquid phase comprising the alcohol, which liquid phase comprises 1 wt. % water or less.

9. The method according to claim 7, wherein the alcohol is selected from the group of primary alkyl alcohols, secondary alkyl alcohols, optionally substituted aryl alcohols and optionally substituted aralkyl alcohols.

10. The method according to claim 7, wherein the prepared C-terminal ester is an activated ester, suitable for coupling another amino acid or peptide to the amino acid or peptide by kinetic peptide coupling.

11. The method according to claim 1, wherein the transesterification is conducted to at least 70%, of the C-terminal t-alkyl ester having been transesterified.

12. The method according to claim 7, wherein the t-alkyl is selected from the group of t-butyl, t-pentyl and t-hexyl.

13. The method according to claim 1, wherein a peptidase is used selected from the group of carboxylic ester hydrolases, thiolester hydrolysases, lipases and peptidases.

14. The method according to claim 13, wherein the enzyme is a peptidase selected from the group of serine carboxypeptidases, metallocarboxypeptidases, cysteine carboxypeptidases, serine endopeptidases, cysteine endopeptidases, aspartic endopeptidases and metalloendopeptidases.

15. The method according to claim 14, wherein the serine endopeptidase is a subtilisin.

16. A method for preparing a peptide comprising coupling an activated, N-protected, amino acid C-terminal ester or an activated, optionally N-protected, peptide C-terminal ester, the coupling comprising
activating a t-alkyl C-terminal ester of a first N-protected amino acid or a t-alkyl C-terminal ester of a first, optionally N-protected, peptide, which C-terminal t-alkyl ester is selected from the group of t-butyl esters, t-pentyl esters and t--hexyl esters, by transesterification with an activating alcohol wherein the activating alcohol is selected from the group of optionally substituted n-alkyl alcohols, optionally substituted aralkyl alcohols and optionally substituted aryl alcohols, the activation being catalysed by a subtilisin (EC. 3.4), thereby forming a second N-protected amino acid C-terminal ester or a second, optionally N-protected, peptide C-terminal ester; and
wherein the activation respectively transesterification take place in a liquid phase comprising the activating alcohol, which liquid phase comprises less than 1 wt. % water, based on the total weight of the liquid phase; and
coupling the second ester with an, optionally C-terminal protected, amino acid or an, optionally C-terminal protected, peptide forming a peptidic bond, the coupling being catalysed by an enzyme catalysing peptidic bond formation, which enzyme may be the same as or different from the enzyme used for catalysing the transesterification.

* * * * *